United States Patent
den Hartog et al.

(10) Patent No.: US 6,263,042 B1
(45) Date of Patent: Jul. 17, 2001

(54) APPARATUS FOR X-RAY ANALYSIS IN GRAZING EXIT CONDITIONS

(75) Inventors: Sander G. den Hartog; Pieter K. de Bokx, both of Eindhoven (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/406,285

(22) Filed: Sep. 24, 1999

(30) Foreign Application Priority Data

Sep. 28, 1999 (EP) .................................................. 98203223

(51) Int. Cl.$^7$ ................................................. G01N 23/223
(52) U.S. Cl. .................................. 378/44; 378/45; 378/49
(58) Field of Search .................................. 378/44, 45, 46, 378/49, 83, 84

(56) References Cited

U.S. PATENT DOCUMENTS

| | | | |
|---|---|---|---|
| 5,497,008 | 3/1996 | Kumakhov | 250/505.1 |
| 5,684,857 | * 11/1997 | De Bokx | 378/44 |
| 5,742,658 | * 4/1998 | Tiffin et al. | 378/44 |
| 5,778,039 | * 7/1998 | Hossain et al. | 378/44 |

FOREIGN PATENT DOCUMENTS

| 5-126768 | * 5/1993 | (JP) | 378/44 |
|---|---|---|---|
| WO9713142 | 4/1997 | (WO) | G01N/23/207 |

* cited by examiner

*Primary Examiner*—Drew Dunn

(57) ABSTRACT

In order to achieve suitable positional resolution for an angular scan in Grazing Exit X-ray Fluorescence (GEXRF), the sample (2) should be irradiated with a small spot (14). Consequently, the fluorescent radiation yield is low so that the duration of a measurement is comparatively long. In order to mitigate this drawback, the invention proposes the use of an analyzing X-ray mirror (16) having a line focus (22) extending perpendicularly to the sample surface (4). The line focus (22) coincides with a line-shaped PSD (24), so that every position on the PSD corresponds to a given height on the mirror, which height itself corresponds to a given take-off angle of the fluorescent radiation relative to the sample surface. Excellent positional resolution and an attractive fluorescent radiation yield are obtained by irradiating the sample by way of a focused electron beam.

6 Claims, 1 Drawing Sheet

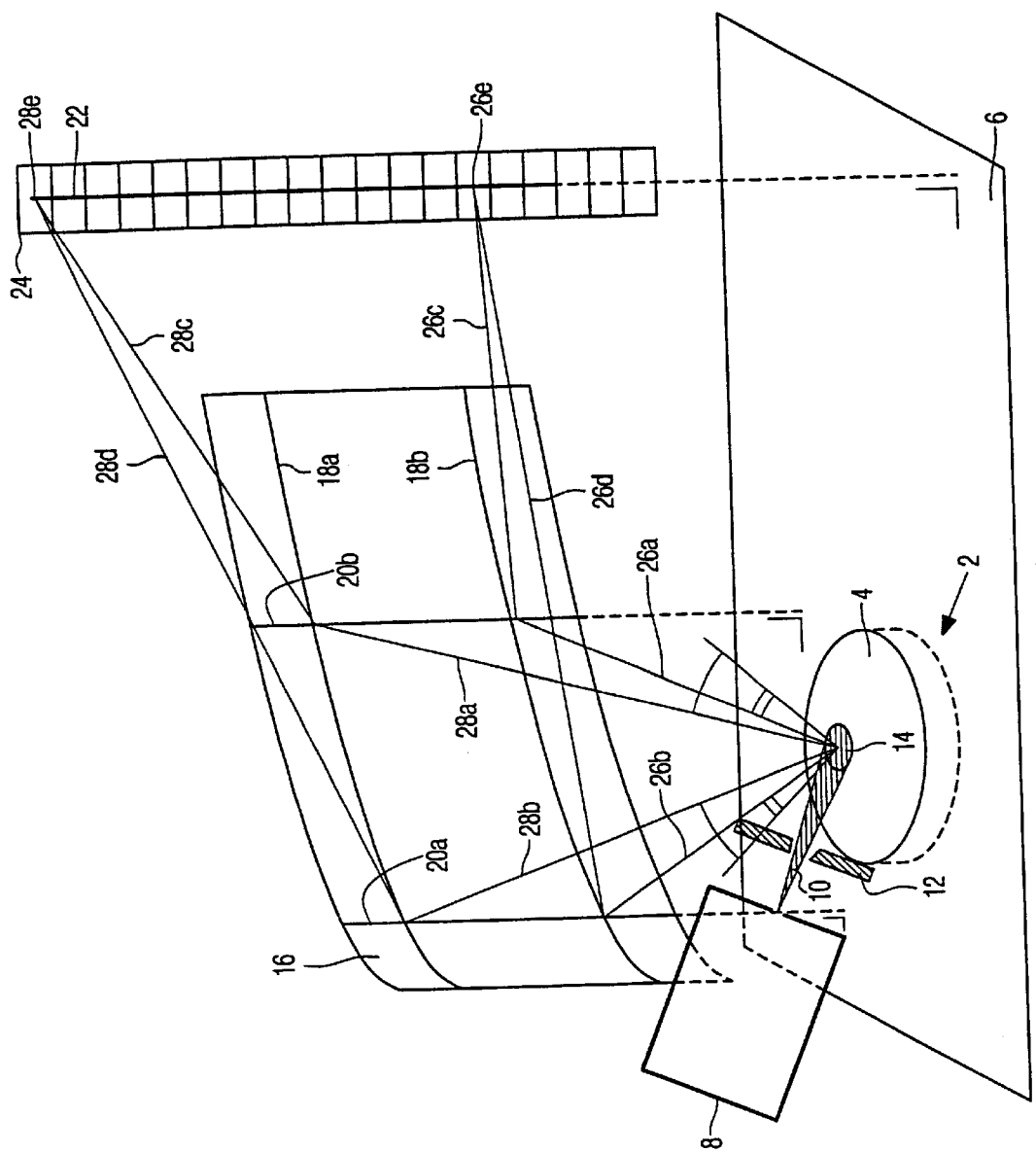

APPARATUS FOR X-RAY ANALYSIS IN GRAZING EXIT CONDITIONS

FIELD OF THE INVENTION

The invention relates to an apparatus for X-ray analysis, including a sample location for accommodating a sample to be analyzed, means for generating X-rays in the sample, a position-sensitive detector for detecting X-rays generated in the sample, a focusing X-ray mirror which is arranged in the beam path between the sample and the detector in order to focus X-rays emanating from the sample on the detector in the form of a line focus, the detector and the X-ray mirror being arranged relative to one another in such a manner that a position-sensitive direction of the detector extends parallel to the line focus.

An apparatus of this kind is known from the published international patent application No. WO 97/13142. The X-ray analysis apparatus disclosed therein includes a fluorescence unit with a focusing X-ray mirror and a position-sensitive detector (PSD) for detecting fluorescent radiation generated in a sample to be examined. The beam of fluorescent radiation emanating from the exposed area on the specimen diverges in two directions (in the plane of drawing as well as in the direction perpendicular thereto). This beam is captured by the focusing X-ray mirror whose surface is shaped as a cylinder at that area. By virtue of this shape it is achieved that the beam is focused to a given extent, so that a significant part of the beam lands on the PSD. The focusing X-ray mirror then serves as an analysis element, i.e. every position on the PSD corresponds to a given position on the mirror, which itself corresponds to a given wavelength of the fluorescent radiation.

The (known) operation of such an analysis element (usually a monocrystal or a multilayer mirror which is known per se) is based inter alia on the well-known Bragg relation $2d.\sin \vartheta = n\lambda$ (d=spacing of the reflecting planes of the crystal or the mirror, $\vartheta$=angle of incidence of the X-rays on the reflecting planes, n=the order of the reflection, and $\lambda$=the wavelength of the X-rays). This relation demonstrates that only radiation which is incident on the analysis element at the correct angle $\vartheta$ is reflected.

Because of the proportioning and the positioning of the X-ray mirror relative to the sample in the known apparatus, a relation exists between the reflected wavelength and the position on the PSD. The intensity of the incident radiation is determined in each element of the PSD; thus, reading out all elements of the array yields the intensity spectrum as a function of the wavelength of the fluorescent radiation.

In contemporary X-ray analysis there is a need for determination of the properties of thin layers on a sample, such as the layer thickness and the concentration of a given chemical element in a layer of an integrated electronic circuit (IC). To this end, according to a generally known method the sample is irradiated by means of exciting radiation so that fluorescent radiation is generated in the sample. Information concerning said layer properties can be acquired by measurement of the fluorescent radiation. However, using the conventional X-ray fluorescence (XRF) method, one measurement can yield only information concerning the product of the concentration and the layer thickness, but no information concerning each of these quantities individually. The latter information can be acquired by means of an existing detection method which is known as Grazing Exit XRF (GEXRF). In the case of GEXRF the sample (for example, an IC) has a smooth and plane surface. The intensity of the fluorescent radiation of one given, desired wavelength (notably a characteristic wavelength of a chemical element which is relevant to the analysis) is then measured as a function of the exit angle relative to the surface of the sample; in this respect only small exit angles (Grazing Exit) are of importance, i.e. angles of the order of magnitude of from 0° to approximately 7°. In order to measure the intensity variation as a function of the exit angle, it is necessary to scan the angular range by means of a slit which must be very narrow because of the very severe requirements imposed on the angular resolution in the case of GEXRF. Consequently, this narrow slit transmits only a low X-ray power, so that the duration of the measurement is comparatively long. This is a drawback, notably because such measurements will usually be performed for the manufacture of ICs where the throughput time in the (comparatively expensive) dust-free manufacturing rooms represents an important production factor.

Because of the tendency towards the study of samples with ever smaller details, as is the case for ICs, there is also a need for realizing a high positional resolution in GEXRF. This would be possible only by measuring exclusively the fluorescent radiation originating from the desired small region on the sample, which means that fluorescent radiation is generated only in said small region. However, this has the drawback that the overall power of the fluorescent radiation is also significantly reduced, so that these measurements would require even more time. The gravity of this problem will be illustrated on the basis of the following numerical example.

X-rays are generated in a conventional X-ray tube X-rays while assuming that the X-ray power $P_x$ delivered by the anode is proportional to the electric power $P_e$ taken up by the tube with a proportionality factor c; this can be written as $P_x = c.P_e$. The anode emits this X-ray power in a solid angle $2\pi$ (i.e. in a semi-sphere). If only a part in a solid angle $\Omega$ thereof s used, the X-ray power obtained must be multiplied by $\Omega/(2\pi)$ in order to obtain the useful X-ray power $P_s$ in the sample region of interest. This can be written in the form of a formule:

$$P_s = \frac{cP_e\Omega}{2\pi} \quad (1)$$

Some possibilities for forming an exciting spot on the sample can now be compared; the proportionality factor c is then irrelevant, because its value is the same for all possibilities considered.

For a conventional fluorescent tube it holds that $\Omega=1.6$ staradian. This value has been determined on the basis of the fact that the X-ray beam formed by such a tube typically has half an angle of aperture $\alpha$ amounting to approximately 41.5°; this value of $\Omega$ follows directly therefrom according to the relation $\Omega=2\alpha(1-\cos\alpha)$. Using a typical value $P_e=4$ kW, it follows therefrom that $P_s=10^3$ c.

In order to realize the desired small exciting spot (for example, of the order of magnitude of 1 mm), the use might be considered of a microfocus tube which typically has a focal spot of approximately 50 $\mu$m on the anode and an electric power $P_e$ amounting to 40 W. In this tube the distance from the focal spot to the sample typically amounts to 22 mm, resulting in a solid angle value $\Omega$ of $1.6\times10^{-3}$ staradian for a desired spot size of 1 mm. Using the values thus determined there is obtained $p_s=10^{-2}$ c, being $10^5$ times smaller than that for a conventional fluorescent tube. It will be evident from the foregoing numerical examples that this choice does not offer a solution to the described problem concerning the long measuring times.

SUMMARY OF THE INVENTION

The apparatus which is known from said international patent application does not offer a solution to these problems either, because this apparatus is arranged to execute a wavelength-dispersive measurement and not to execute an angular scan.

It is an object of the invention to provide an X-ray analysis apparatus which is suitable for picking up an intensity distribution of fluorescent radiation as a function of the exit angle in GEXRF conditions, without the measuring times becoming inadmissibly long.

To achieve this, the apparatus of the kind set forth is characterized in that the X-ray mirror is proportioned and arranged relative to the surface of the sample in such a manner that the mirror captures the X-rays which emanate from the sample surface in grazing exit conditions, and that the direction of the line focus extends transversely of the sample surface.

Because the X-ray mirror must have a wavelength-selective effect for the desired wavelength, the desired wavelength must be received on the mirror surface at the correct angle so that the mirror surface must be arranged so as to be correctly oriented relative to the spot on the sample. Because the non-curved direction of the mirror surface extends transversely of the sample surface, correspondence exists between the height of incidence on the mirror and the take-off angle of the fluorescent radiation. Consequently, in the focal line (the line focus) formed by the mirror there is also correspondence between the position in the focal line and the take-off angle. When the focal line is made coincident on the PSD, each element of the PSD will correspond to a given take-off angle of the radiation, so that the intensity distribution is picked up as a function of the take-off angle in a non-sequential manner (so during one exposure).

The X-ray mirror should preferably be proportioned such that the height of the mirror (i.e. the dimension of the mirror in the direction perpendicular to the sample surface or, in other words, the dimension in the non-curved direction of the mirror) suffices to capture all grazing exit fluorescent radiation, i.e. all radiation emanating from the sample surface with an angle of between 0°, so parallel to the surface, and an angle which is dependent on the layer thickness and the chemical elements present in the relevant layer, but is generally smaller than 10°.

In one embodiment of the invention the means for generating X-rays in the sample are formed by the combination of an X-ray tube and a unit for capillary X-ray optics.

Using such a combination, the problem concerning the low power of the fluorescent radiation can be mitigated in that the capillary X-ray optics can be used to conduct the often very diverging X-rays from the X-ray tube, via the capillary tubes conducting the X-rays, to the region of the sample to be irradiated, thus forming a small spot of comparatively high intensity. Such capillary structures for the manipulation of X-rays are known per se, for example from U.S. Pat. No. 5,497,008.

In another embodiment of the invention, the means for generating X-rays in the sample are formed by an X-ray tube which is arranged to form a line-shaped focal spot on the anode of the X-ray tube. Because of its use in X-ray diffraction, a tube having a line-shaped focal spot is generally referred to as a diffraction tube. The advantage of the use of a diffraction tube for GEXRF can be illustrated on the basis of the above expression (1) while using typical numbers for such a tube. A diffraction tube is assumed to have a focal line on the anode having the dimensions 1×10 mm. When a round diaphragm, having a diameter of 0.66 mm, is arranged at a distance of 10 mm from the anode, on the sample, situated at a distance of 15 mm from the anode, there is formed an X-ray spot having a diameter of approximately 1 mm. It can be readily seen that only a part of approximately 2.5 mm (so a surface of 2.5 cm$^2$) of the overall focal line contributes to a spot on the sample. A typical value of the electric power of such a tube is 480 W/mm$^2$, so that in this case $P_e$=1.2 kW. For the above geometry, it holds that the space angle $\Omega$=0.6×10$^{-3}$ staradian. Using these numbers, the expression (1) yields a value $P_s$=0.66 c, so approximately 1500 times less than in the case of irradiation of the sample by means of the conventional fluorescent tube having the large spot. Because the angular scan according to the invention is performed in one operation, the lower X-ray power in the exciting beam is compensated by the gain in time of the non-sequential angular scan.

In a preferred embodiment of the invention, the means for generating X-rays in the sample are formed by an electron source which is arranged to irradiate the sample by means of an electron beam.

Fluorescent radiation can be generated not only by irradiating the sample by means of (primary) X-rays, but also by excitation of the atoms in the sample by means of electrons. The major advantage of excitation by means of an electron beam resides in the fact that a very small exciting spot can be very simply realized by means of such a beam. In this respect a typical spot dimension of the order of magnitude of from 10 nm to some hundreds of nm and a beam current of the order of magnitude of 10 nA are feasible. Comparison of the current in an X-ray tube with the current in an electron beam enables an estimate to be made of the X-ray power released in a sample by a focused electron beam. Such an (approximative) calculation results in a fluorescent radiation yield with a power which is approximately ten times higher than in the case of said diffraction tube; the use of an electron beam also offers the advantage that the exciting spot is many times smaller (and hence the positional resolution is substantially higher) than in the case of excitation by means of X-rays.

In a further embodiment of the invention, the means for generating X-rays in the sample are arranged in such a manner that the spot in which the X-rays are generated in the sample is smaller than 3% of the distance from the spot to the X-ray mirror.

A calculation demonstrates that in the case of such a dimension of the spot, an angular resolution of the order of magnitude of 3 mrad can be achieved, it being assumed that the angular range of the angular scan is 100 mrad.

For GEXRF measurements, where a slit is scanned across the angular range to be measured (so during a sequential measurement), an angular resolution of approximately 1 mrad can be achieved while the measuring times remain acceptable nevertheless. It is notably attractive if the same angular resolution and a measuring time which is still acceptable could also be achieved by means of the present invention. Therefore, in a further embodiment of the invention the dimension of the spot is less than 1% of said distance.

BRIEF DESCRIPTION OF THE DRAWING

The invention will be described in detail hereinafter with reference to the sole FIGURE. The FIGURE shows diagrammatically the relevant parts of an GEXRF apparatus for carrying out the invention.

DETAILED DESCRIPTION OF THE PREFERRED EMBODIMENTS

A sample 2 to be examined is arranged in the apparatus shown in the FIGURE. The sample may be formed by an electronic integrated circuit (IC) or another type of sample. It is important that the sample has a flat and smooth surface 4, because the angle for grazing exit cannot be suitably defined in the case of a rough and/or curved surface. The surface 4 of the sample is situated in an imaginary flat plane which is denoted by the reference numeral 6 in the FIGURE.

X-rays are generated in the sample 2. These X-rays are generated by means of suitable means 8, for example an X-ray tube or an electron source. When use is made of an X-ray tube, the tube may an X-ray diffraction tube as marketed by Philips. Such a tube typically has an electric power of 2.2 kW and a focal line of 1×10 mm on the anode. The exciting X-rays (also referred to as primary X-rays) leave the X-ray tube in the form of an X-ray beam 10. This beam is stopped to the desired cross-sectional dimension by a diaphragm 12 which has a round aperture of, for example 0.66 mm. The diaphragm is situated at a distance of 10 mm from the anode. A round region to be irradiated (the X-ray spot 14) is thus formed on the sample, said spot having a diameter of 1 mm. The primary X-rays generated in the tube are polychromatic X-rays, i.e. rays consisting of an X-ray continuum on which the spectral X-ray lines which are characteristic of the anode material of the tube are superposed. These primary polychromatic X-rays thus form a spot on the region to be irradiated on the sample 2.

When the X-rays are generated in the sample by means of an electron beam 10, any electron source can be employed, for example as also used in electron microscopes. The electron beam can be focused by means of a set of conventional electron lenses as also used in electron microscopes. In that case no beam limiting diaphragm is required so as to define the diameter of the spot 14 on the sample. In the case of a focused electron beam this diameter is determined by the physical dimensions of the electron source and by the magnification and the lens defects of the focusing lens system. Depending on the type of electron source and the quality of the lenses, such a spot may have a dimension of from 10 nm to some hundreds of nm. When the fluorescent radiation is generated by means of an electron beam, the part of the analysis apparatus in which free electrons travel (i.e. the space from the cathode of the electron source to the sample) should be evacuated. This is also the case when soft fluorescent radiation is to be detected.

The fluorescent radiation generated in the sample 2 by the primary radiation or the electron beam in principle propagates in all directions. For GEXRF only the directions which enclose a small angle (up to 100 mrad) relative to the surface of the sample are of importance. A part of the fluorescent radiation emanating in this angular range is captured by a curved focusing X-ray mirror 16.

The curved focusing X-ray mirror may be constructed as a curved monocrystal or as a known, artificially manufactured multilayer mirror. This mirror is curved in a plane extending parallel to the plane 6, i.e. the intersection of the mirror surface and a plane extending parallel to the plane 6 constitutes a curved line. Curved lines of this kind are denoted by the references 18a and 18b in the FIGURE. As is known from X-ray fluorescence, in dependence on the requirements imposed as regards the sharpness of the focal line formed by the curve and on the wavelength selectivity, the shape of these curves may be that of a logarithmic spiral, a circle or any suitable approximation of such shapes.

The mirror 16 is not curved in a plane extending perpendicularly to the plane 6, i.e. the intersection of the mirror surface and a plane extending transversely of the plane 6 forms a straight line. Such straight lines are denoted by the references 20a and 20b in the FIGURE. As is indicated in the FIGURE, these lines extend perpendicularly to the plane 6 and hence perpendicularly to the sample surface 4.

The fluorescent radiation emanating from the spot 14 is focused by the mirror 16 so as to form a line focus 22. A position-sensitive detector 24 is arranged in the position in which the line focus 22 is formed. PSDs of this kind are known from the X-ray analysis technique and need not be elaborated herein. A PSD is composed of a stack of PSD elements, each of which is individually sensitive to X-rays. The intensity of the X-rays incident on an element is determined per element. In this case the position-sensitive direction of the PSD is the direction of the line focus, so the direction of stacking of the PSD elements. This position-sensitive direction of the PSD extends perpendicularly to the plane 6, as shown in the FIGURE, and hence also perpendicularly to the sample surface 4.

In order to explain the operation of the apparatus according to the invention, a number of rays can be distinguished in the fluorescent radiation emanating from the spot 14. The rays 26a and 26b emanate from the sample surface 4 at the same angle, but with mutually different directions in the exit plane. The ray 26a is reflected by the mirror 16 as a ray 26c in the direction of the PSD 22 where this ray is incident on a PSD element 26e. The mirror 16 reflects the ray 26b as a ray 26d in the direction of the PSD 22 where it also is incident on the PSD element 26e. The mirror 16 reflects the ray 28a as a ray 28c in the direction of the PSD 22 where it is incident on the PSD element 28e. The mirror reflects the ray 28b as a ray 28d in the direction of the PSD 22 where this ray is also incident on the PSD element 28e. This means that rays which leave the sample surface 4 at the same angle are reflected to the same PSD element. An intensity distribution can thus be determined as a function of the take-off angle.

What is claimed is:

1. An X-ray analysis apparatus which includes
   a sample location for accommodating a sample (2) to be analyzed,
   means (8) for generating X-rays in the sample,
   a position-sensitive detector (24) for detecting X-rays generated in the sample (2),
   a focusing X-ray mirror (16) which is arranged in the beam path between the sample (2) and the detector (24) in order to focus X-rays emanating from the sample on the detector (24) in the form of a line focus (22),
   the detector (24) and the X-ray mirror (16) being arranged relative to one another in such a manner that a position-sensitive direction of the detector extends parallel to the line focus (22), characterized in that
   the X-ray mirror (16) is proportioned and arranged relative to the surface (4) of the sample (2) in such a manner that the mirror (16) captures the X-rays which emanate from the sample surface (4) in grazing exit conditions, and that the direction of the line focus (22) extends transversely the sample surface (4).

2. An X-ray analysis apparatus as claimed in claim 1, in which the means (8) for generating X-rays in the sample (2) are formed by the combination of an X-ray tube and a unit for capillary X-ray optics.

3. An X-ray analysis apparatus as claimed in claim 1, in which the means (8) for generating X-rays in the sample (2)

are formed by an X-ray tube which is arranged to form a line-shaped focal spot on the anode of the X-ray tube.

4. An X-ray analysis apparatus as claimed in claim 1, in which the means (8) for generating X-rays in the sample (2) are formed by an electron source which is arranged to irradiate the sample by means of an electron beam (10).

5. An X-ray analysis apparatus as claimed in claim 1, in which the means (8) for generating X-rays in the sample are arranged in such a manner that a spot (14) in which the X-rays are generated in the sample is smaller than 3% of the distance from the spot to the X-ray mirror (16).

6. An X-ray analysis apparatus as claimed in claim 5, in which the dimension of the spot is less than 1% of said distance.

* * * * *